US00PP17254P2

(12) United States Plant Patent
Bradford

(10) Patent No.: US PP17,254 P2
(45) Date of Patent: Dec. 5, 2006

(54) NECTARINE TREE NAMED 'MAY PEARL'

(50) Latin Name: *Prunus persica*
Varietal Denomination: MAY PEARL

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 44 days.

(21) Appl. No.: 11/311,172

(22) Filed: Dec. 20, 2005

(51) Int. Cl.
*A01H 5/00* (2006.01)

(52) U.S. Cl. ..... Plt./188
(58) Field of Classification Search ..... Plt./188
See application file for complete search history.

(56) References Cited

U.S. PATENT DOCUMENTS

PP7,421 P 1/1991 Bradford
PP9,360 P 11/1995 Bradford
PP14,248 P2 10/2003 Bradford

*Primary Examiner*—Kent Bell
*Assistant Examiner*—Annette H Para

(57) ABSTRACT

The present invention relates to a nectarine tree and more particularly to a new and distinct variety broadly characterized by a medium size, vigorous, half-hardy, self-fertile, productive and regular bearing tree. The fruit matures under the ecological conditions described in mid May, with first picking on May 17, 2005 . The fruit is uniformly medium in size, excellent in flavor, globose to slightly oblong in shape, clingstone in type, firm in texture, white in flesh color, and mostly red in skin color. The variety was developed as a first generation cross using 'June Pearl' (U.S. Plant Pat. No. 9,360) white flesh nectarine as the selected seed parent and 'Rose Diamond' (U.S. Plant Pat. No. 7,421) as the selected pollen parent.

1 Drawing Sheet

Botanical classification: *Prunus persica.*
Variety denomination: 'May PEARL'.

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of nectarine tree, which has been denominated varietally as 'May PEARL'. The present variety was hybridized by me in 1999, grown as a seedling on its own root in my greenhouse, and transplanted to a cultivated area of my experimental orchard at Bradford Farms near La Grand, Calif. in Merced County (San Joaquin Valley).

The variety was developed as a first generation cross using 'June Pearl' (U.S. Plant Pat. No. 9,360) white flesh nectarine as the selected seed parent and 'Rose Diamond' (U.S. Plant Pat. No. 7,421) as the selected pollen parent. A single tree from the stated cross was selected as the claimed variety. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, 'June Pearl' (U.S. Plant Pat. No. 9,360) nectarine, by producing white flesh nectarines that are firm in texture, sub-acidic and sweet in flavor, clingstone in type, and mostly red in skin color, but is very distinguished therefrom by producing fruit that matures about 3 weeks earlier.

The present variety is very distinguished from its pollen parent, 'Rose Diamond' (U.S. Plant Pat. No. 7,421) nectarine, by producing nectarines that are white instead of yellow in flesh color, that are sub-acid instead of acid in flavor, and that mature about nine days earlier.

The present variety is most similar to 'Early Pearl' (U.S. Plant Pat. No. 14,248) nectarine, by producing nectarines that are firm in texture, sub-acidic and sweet in flavor, clingstone in type, mostly red in skin color, and white in flesh color, but is distinguished therefrom by having a much larger blossom with a higher percentage of double blossoms, by requiring much less chilling, and by producing fruit that matures about ten days earlier.

SUMMARY OF VARIETY

In summary, the present variety is characterized by a medium size, vigorous, half-hardy, self-fertile, productive and regular bearing tree. The fruit matures under the ecological conditions described in mid May, with first picking on May 17, 2005. The fruit is uniformly medium in size, excellent in flavor, globose to slightly oblong in shape, clingstone in type, firm in texture, white in flesh color, and mostly red in skin color.

DRAWING

The accompanying photograph exhibits four whole fruits positioned to display the characteristics of the skin color and form, one fruit divided transversely to the suture plane to reveal the flesh and stone, a typical leaf, a tip shoot with varying stages of leaf development, and several stages of buds and flowers in the upper insets.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of full ripe on May 22, 2005, on the original tree during its sixth growing season. All major color code designations are by reference to the Inter-Society Color Council, National Bureau of Standards. Common color names are also used occasionally.

TREE

Size: Medium, reaching a height of 11' [3.35 m.] and a spread of 8' [2.44 m.] after six growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Upright and dense.

Form: Round topped.

Hardiness: Half-hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Approximate chilling requirement: 400 hours.

Trunk:

*Size.*—Medium, with a maximum diameter of 3⅛" [79 mm.] after the sixth growing season.

*Texture.*—Somewhat shaggy.

*Bark color.*—A two-tone variegation of Grayish brown [61. gy.Br] and Deep brown [56. deep Br].

*Lenticels.*—Approximate Number Per Square Inch: 10. Color: Strong yellowish brown [74. s.yBr]. Typical Size: ⅛" to 7⁄16" [3.2–11.1 mm.]. Shape: Eye-shaped to elongated.

Branches:

*Size.*—Diameter of limb is 1½" [38 mm.] measured 12" above the crotch, 1" [25 mm.] measured 12" above the secondary fork.

*Texture.*—Smooth on 1st year wood, increasing roughness with age.

*Color.*—1st Year Wood Topside: Grayish red [19. gy.R]. 1st Year Wood Underside: Strong yellow green [117. s.YG]. Older Wood: Moderate brown [58. m.Br].

*Lenticels.*—Approximate Number Per Square Inch: 50. Color: Light yellowish brown [76. l.yBr]. Typical size: 1⁄64" [0.4 mm.] to ⅛" [3.2 mm.]. Shape: Eye-shaped to elongated.

Leaves:

*Size.*—Medium. Average Length: 5½" [139.7 mm.]. Average Width: 1⅝" [41.3 mm.].

*Arrangement.*—Alternate.

*Thickness.*—Medium.

*Form.*—Elliptical.

*Apex.*—Acuminate.

*Base.*—Rounded.

*Surface.*—Smooth.

*Color.*—Dorsal Surface: Dark yellowish green [137. d.yG]. Ventral Surface: Moderate yellowish green [136. m.yG].

*Margin.*—Finely serrate.

*Venation.*—Pinnately net veined.

*Vein color.*—Light yellow green [119. l.YG].

*Petiole.*—Average Length: ⅜" [9.5 mm.]. Average Thickness: 1⁄16" [1.6 mm.]. Color: Brilliant yellow green [116. brill.YG].

*Stipules.*—Number: 2 to 6 per growing tip. Average Length: 5⁄16" [7.9 mm.]. Color: Brilliant yellow green [116. brill.YG] turning Moderate reddish orange [37. m.rO] with maturity and becoming Dark reddish brown [44. d.rBr] when dried.

*Glands.*—Number: 2 to 6, usually 2. Position: Usually alternate, located at the intersection of petiole and base of blade. Size: Small. Form: Globose. Color: Brilliant yellow green [116. brill.YG] turning Grayish brown [61. gy.Br] in the center with maturity.

*Leaf buds.*—Pointed, Medium.

Flower buds:

*Hardiness.*—Hardy, with respect to central California winters.

*Diameter.*—Typically ⅜" [9.5 mm.] 1 week before bloom.

*Length.*—Typically 9⁄16" [14.3 mm.] 1 week before bloom.

*Form.*—Not appressed.

*Surface.*—Pubescent.

*Color.*—Moderate purplish red [258. M.pR].

Flowers: Perfect, complete, perigynous, usually a single pistil, typically thirty or more stamens, five sepals and petal locations alternately positioned.

*Type.*—Showy, very large.

*Average flower diameter.*—2⅛" [54.0 mm.].

*Number of petals.*—Five to twelve observed with about forty percent five and forty percent ten.

*Petal shape.*—Circular to oval.

*Petal margin.*—Somewhat wavy.

*Average petal diameter.*—⅞" [22.2 mm.].

*Average petal length.*—⅞" [22.2 mm.].

*Petal apex.*—Rounded.

*Petal base.*—Irregularly rounded.

*Petal color.*—Moderate purplish pink [250. m.pPk] becoming lighter with increased bloom duration.

*Anther color.*—Dark red [16. d.R] over Pale yellow [89. p.Y] centers at bloom onset.

*Stigma color.*—Light greenish yellow [101. l.gY].

*Sepal color.*—Dark purplish red [259. d.pR].

*Sepal length.*—¼" [6 mm.].

*Sepal width.*—3⁄16" [5 mm.].

*Average pistil length.*—⅝" [15.9 mm.].

*Average stamen length.*—⅝" [15.9 mm.].

*Fragrance.*—Moderate.

*Blooming period.*—Early compared with other varieties.

*Onset of bloom.*—One percent on Feb. 7, 2005.

*Date of full bloom.*—Feb. 16, 2005.

*Duration of bloom.*—One to two weeks, dependent on ambient temperature.

*Number per cluster.*—1 to 3 with single flowers most common.

FRUIT

Maturity when described: Full ripe, May 22, 2005.
Date of first picking: May 17, 2005.
Date of last picking: May 24, 2005.
Size: Uniform, medium.
*Average diameter axially.*—2⅝" [66.7 mm.].
*Average diameter across cheek plane.*—2⅝" [66.7 mm.].
*Average diameter across suture plane.*—2 9/16" [65.1 mm.].
*Typical weight.*—5.5 ounces [156 grams].
Form: Mostly uniform, symmetrical, usually globose with a few slightly oblong.
*Longitudinal section form.*—Round to somewhat oval.
*Axial view form.*—Round.
Suture: A shallow but somewhat sharp groove near the base, a shallow trough along the side, and a sharp groove near the apex discontinuing just past the pistil point with a slight depression beyond the pistil point.
Ventral surface: Rounded, lipped stronger toward the apex.
Lips: Fairly equal.
Cavity: Flaring, rounded, elongated in the suture plane, suture showing on one side, Pale greenish yellow [104. p.gY] stem markings typical.
*Depth.*—5/16" [7.9 mm.].
*Breadth.*—⅞" [22.2 mm.].
Base: Rounded to somewhat truncate, slightly cordate if viewed parallel to suture.
Apex: Rounded.
Pistil point: Both apical and oblique, typically ⅛" [3.2 mm] in length, usually depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Nonastringent.
*Tendency to crack.*—Moderate in wet season.
*Color.*—Primarily dark Red [16. d.R] mottled over Strong reddish orange [35. s.rO] background with some Pale greenish yellow [104. p.gY] streaking near the shoulders and moderate Light orange yellow [70.l.OY] freckling toward the apex.
Flesh:
*Color.*—White [263. White] to Greenish white [153. gWhite] from skin to stone.
*Surface of pit cavity.*—Clingstone with Greenish white [153. gWhite] broken fibers when twisted from stone.
*Amygdalin.*—Slight.
*Juice.*—Abundant.
*Texture.*—Medium, melting.
*Fibers.*—Abundant, fine, tender.
*Ripens.*—Earlier toward the apex.
*Flavor.*—Sub-acidic to slightly acidic, mild and sweet, with an average brix of 16.
*Aroma.*—Moderate.
*Eating quality.*—Very good.

STONE

Type: Clingstone.
Form: Oval.
Hilum: Narrow, oblong.
Base: Acute.
Apex: Rounded to obtuse.
Sides: Equal.
Surface: Horizontally furrowed near the apex and pitted toward the base with two characteristic ridges on each side of dorsal the fin.
Ridges: Jagged toward the apex.
External color: Light yellowish brown [76. l.yBr].
Pit wall color when cracked: Pale orange yellow [73. p.OY].
Cavity surface color: Light yellowish brown [76. l.yBr].
Average pit wall thickness: ¼" [6.4 mm.].
Average width: 1 1/16" [27.0 mm.].
Average length: 1⅝" [41.3 mm.].
Average breadth: ¾" [19.1 mm.].
Tendency to split: Moderate in wet season.
Kernel:
*Form.*—Oval.
*Skin color.*—Yellowish white [92. y.White] when freshly removed.
*Pellicle color.*—Light grayish yellowish brown [79. l.gy.yBr].
*Vein color.*—A barely visible Grayish yellowish brown [80. gy.yBr] when freshly removed.
*Taste.*—Bitter.
*Viable.*—Only by using embryoculture techniques.
*Average width.*—9/16" [14.3 mm.].
*Average length.*—13/16" [20.6 mm.].
*Amygdalin.*—Moderate.

USE

Market: Fresh market and long distance shipping.
Keeping quality: Good. Fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to 'Early Pearl' (U.S. Plant Pat. No. 14,248) nectarine, by producing nectarines that are firm in texture, sub-acidic and sweet in flavor, clingstone in type, mostly red in skin color, and white in flesh color, but is distinguished therefrom by having a much larger blossom with a higher percentage of double blossoms, by requiring much less chilling, and by producing fruit that matures about ten days earlier.

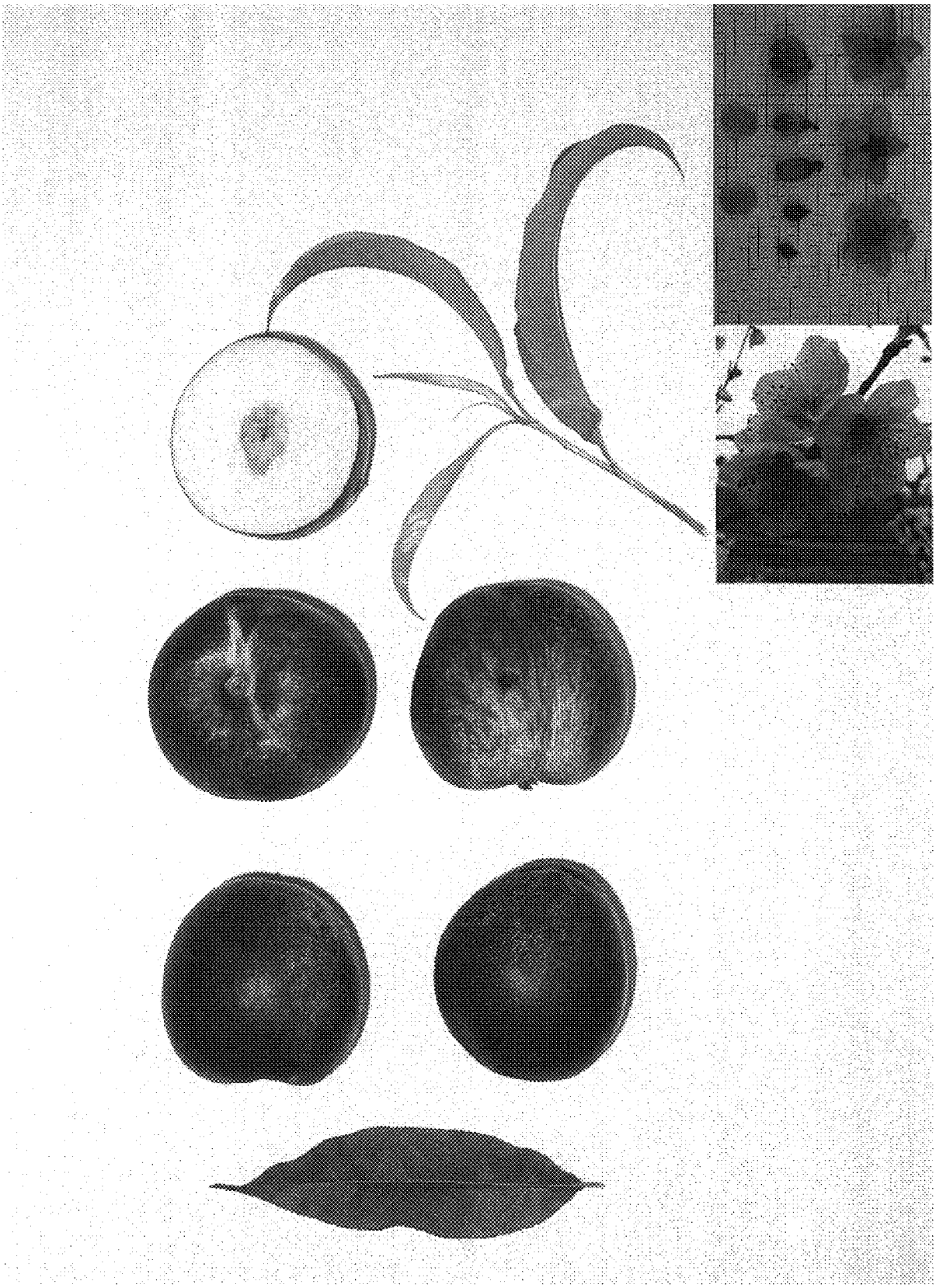

* * * * *